US00PP11975P2

(12) United States Plant Patent
Maiga

(10) Patent No.: US PP11,975 P2
(45) Date of Patent: Jul. 3, 2001

(54) DOUBLE IMPATIENS PLANT NAMED 'CORAL DUET'

(75) Inventor: Bernice A. Maiga, Carson City, MI (US)

(73) Assignee: Good Starts Greenhouse, Carson City, MI (US)

( * ) Notice: Subject to any disclaimer, the term of this patent is extended or adjusted under 35 U.S.C. 154(b) by 0 days.

(21) Appl. No.: 09/320,362

(22) Filed: May 25, 1999

(51) Int. Cl.[7] ..... A01H 5/00

(52) U.S. Cl. ..... Plt./317

(58) Field of Search ..... Plt./317–319

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Double Impatiens plant named 'Coral Duet', characterized by its consistently double flowers that are either coral or light coral pink in color with flowers of both colors on the same plant; upright and mounded plant habit; freely branching; and dark green leaves.

2 Drawing Sheets

BACKGROUND OF THE INVENTION

The present invention relates to a new and distinct cultivar of Double Impatiens plant, botanically known as *Impatiens walleriana*, and hereinafter referred to by the cultivar name Coral Duet.

The new Double Impatiens is a naturally-occurring mutation of an unidentified selection of the seed-grown *Impatiens walleriana* Rosette Mix series (not patented). The new Double Impatiens was discovered and selected by the Inventor in October, 1987, as a flowering plant within a population of plants of the unidentified selection of the Rosette Mix series grown in a controlled environment in Carson City, Mich. The new Double Impatiens was selected on the basis of having both coral and lighter coral pink flowers on the same plant. In addition to the two flower colors on the same plant, plants of the new Double Impatiens are more dwarf and have larger and more numerous flowers than plants of the unidentified selection of the seed-produced Rosette Mix series.

Asexual reproduction of the new cultivar by terminal cuttings taken at Carson City, Mich., has shown that the unique features of this new Double Impatiens are stable and reproduced true to type in successive generations of asexual reproduction.

SUMMARY OF THE INVENTION

The following traits have been repeatedly observed and are determined to be the unique characteristics of 'Coral Duet'. These characteristics in combination distinguish 'Coral Duet' as a new and distinct cultivar:

1. Consistently double flowers that are either coral or light coral pink in color. Plants consistently produce both coral and light coral pink-colored flowers.
2. Upright and mounded plant habit.
3. Freely branching; plants do not require pinching.
4. Dark green leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a top perspective view of a typical plant of 'Coral Duet'.

The photograph at the top of the second sheet comprises a close-up view of a typical plant of 'Coral Duet'.

The photograph at the bottom of the second sheet comprises a close-up view of a typical coral-colored flower (left) and a typical light coral pink-colored flower (right) both taken from a typical plant of 'Coral Duet'. Flower and foliage colors in the photographs may appear different from the actual colors due to light reflectance.

DETAILED BOTANICAL DESCRIPTION

The cultivar Coral Duet has not been observed under all possible environmental conditions. The phenotype may vary somewhat with variations in environment such as temperature and light intensity, without, however, any variance in genotype. The following observations, measurements and comparisons describe plants grown 10-cm pots in Carson City, Mich. and Keller, Tex., under conditions which closely approximate typical commercial practice for Double Impatiens. Plants used for the description were about 10 to 12 weeks old from rooted cuttings.

In the following description, color references are made to The Royal Horticultural Society Colour Chart except where general terms of ordinary dictionary significance are used.

Botanical classification: *Impatiens walleriana* cultivar Coral Duet.

Parentage: Naturally-occurring mutation of unidentified selection of the seed-grown *Impatiens walleriana* Rosette Mix series (not patented).

Propagation:

*Type cutting.*—Terminal cuttings.

*Time to initiate roots.*—About 10 to 14 days at 18° C.

*Time to develop roots.*—About 35 days to 18° C.

*Root description.*—Fibrous, fine, freely branching.

Plant description:

*Plant form.*—Upright and mounded.

*Growth and branching habit.*—Basal branching with about five lateral branches at the base with secondary lateral shoots forming typically at most nodes; plants do not require pinching. Appropriate for 10-cm and larger containers.

*Plant height.*—About 18 cm; larger plants may attain a height of about 30 cm.

*Lateral branches.*—Length: About 13 cm. Diameter: About 7.5 mm. Internode length: About 2.2 cm. Color: 146B to 146C with dark red purple, Close to 59A, longitudinal streaks.

*Foliage description.*—Leaves simple, symmetrical, abundant, alternate. Length: About 4.7 cm. Width: About 3.4 cm. Shape: Ovate. Apex: Sharply acuminate. Base: Obtuse. Margin: Crenate and ciliate. Texture: Smooth, glabrous. Color: Fully expanded foliage, upper surface: Greener than 147A. Fully expanded foliage, lower surface: close to 147B with dulled purple, fainter than 183B, spots. Petiole: Length: About 2.1 cm. Diameter: About 3 mm. Color: Upper surface: Light green, close to 147C. Lower surface: Close to 147C.

Flower description:

*Flower type and habit.*—Consistently double flowers. Flowers can be either coral with faint light coral pink longitudinal streaks or light coral pink with coral longitudinal streaks. Both color types are found consistently on individual plants. Flower buds open similar to a rose in fullness. Freely and continuously flowering. Flowers arise from leaf axils. Usually about four flowers and flower buds per secondary lateral branch. Flowers positioned slightly above the foliage and typically face outward and upright. Flowers not persistent.

*Flowering season.*—Year-round under greenhouse conditions. In the garden, flowering is continuous from spring until fall.

*Flower size.*—Diameter: About 4.3 cm. Depth (height): About 2.1 cm.

*Flower buds.*—Length: About 1.5 cm. Diameter: About 1 cm. Shape: Ovoid. Color: Close to 48C.

*Petals/petaloids.*—Quantity: Numerous, about 25 to 60. Length: About 2.5 cm. Width: About 2.1 cm. Shape: Rounded to slightly cordate. Apex: Rounded or ermarginate. Base: Attenuate. Margin: Entire. Texture: Smooth, satiny. Color: Flowers that are coral with faint light coral pink longitudinal streaks: When opening, upper surface: More intense than a combination of 40A, 43B and 47B with faint light coral pink, close to 47D to 48C to 48D to 49D, longitudinal streaks; iridescent. When opening, lower surface; 48B to 48C with faint light coral pink, close to 48D to 49D, longitudinal streaks; somewhat iridescent. Fully opened, upper surface: More intense than a combination of 40A, 43B and 47B to 47C with faint light coral pink, close to 47D to 48C to 48D to 49D, longitudinal streaks; iridescent. Fully opened, lower surface: Close to 48B to 48D with faint light coral pink, close to 48D to 49D, longitudinal streaks; somewhat iridescent. Flowers that are light coral pink with coral longitudinal streaks: When opening, upper surface: 48C to 48D with coral, 47B to 47C, longitudinal streaks; iridescent. When opening, lower surface: 48D to 49A with coral, 47D to 48B to 48C, margins and longitudinal streaks; somewhat iridescent. Fully opened, upper surface: 49A to 49D with coral, 47B to 47C, longitudinal streaks; iridescent. Fully opened, lower surface: 49C to 49D with coral, 48C to 48D, margins and longitudinal streaks; somewhat iridescent.

*Spurs.*—Length: About 3.4 cm. Diameter: About 1 mm. Color: Initially green, close to 146C, with slight anthocyanin, close to 59A, becoming light pink, 56A, with flower development.

*Peduncles.*—Length: About 3.2 cm. Diameter: About 2 mm. Angle: Upright or outward. Strength: Moderately strong; flexible. Color: 146A to 146C.

*Reproductive organs.*—None have been observed to date.

Disease resistance: Under commercial conditions, resistance to pathogens has not been observed.

Seed development: Seed production has not been observed to date.

It is claimed:

1. A new and distinct cultivar of Double Impatiens plant named 'Coral Duet', as illustrated and described.

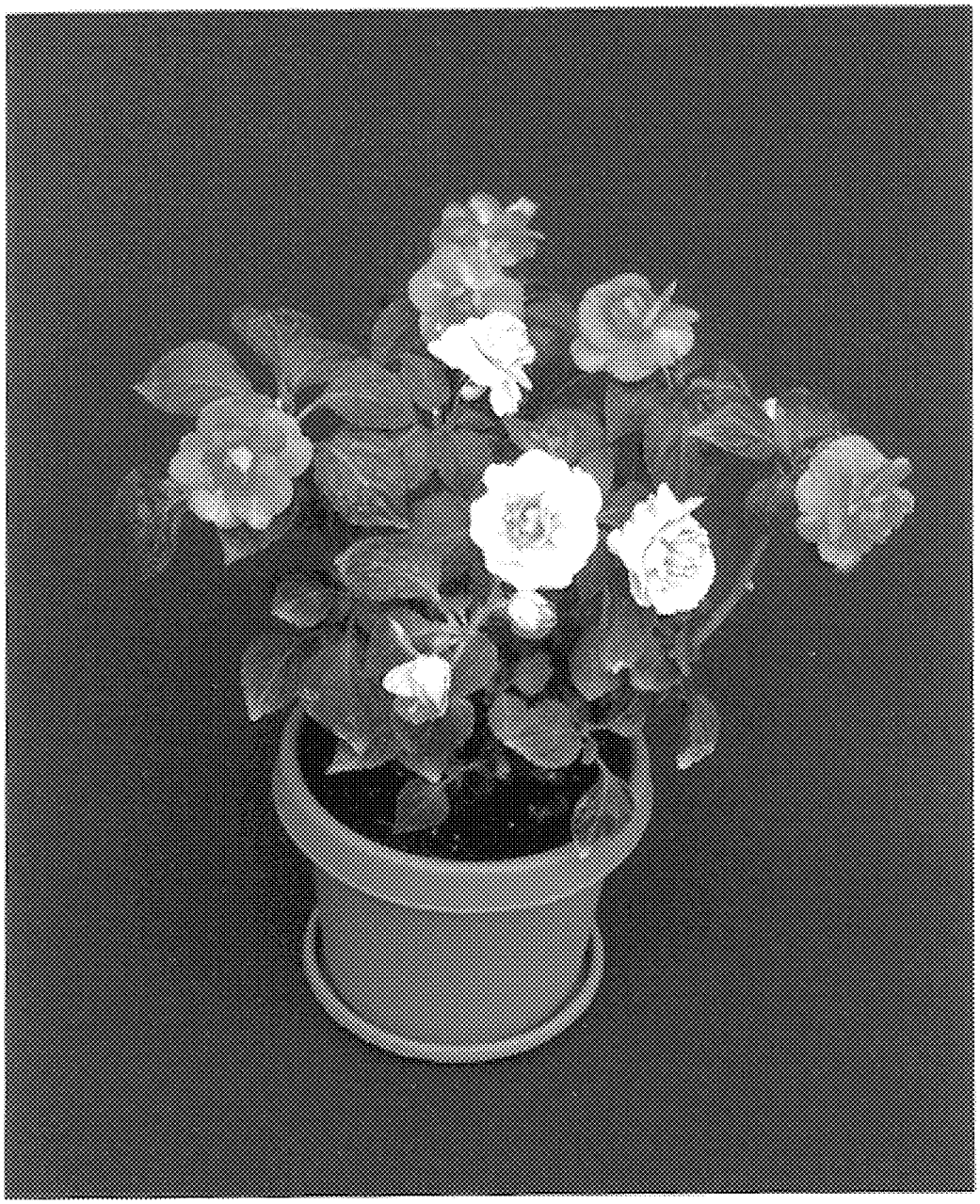

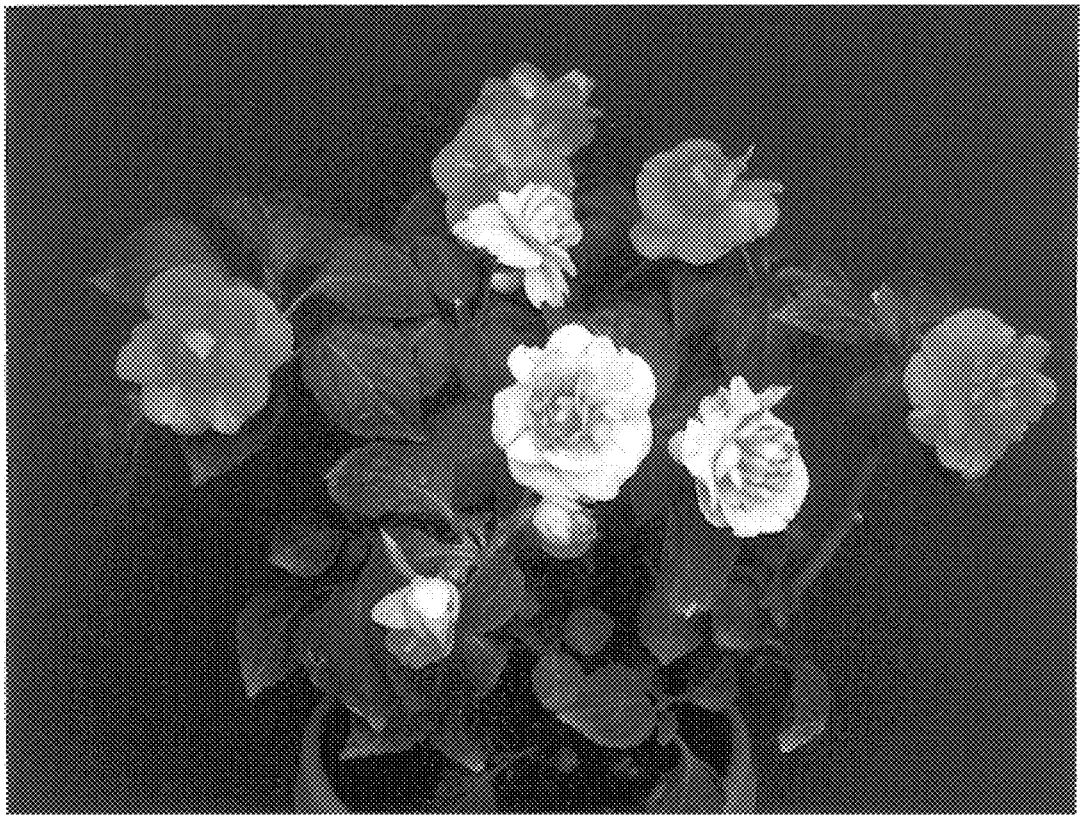
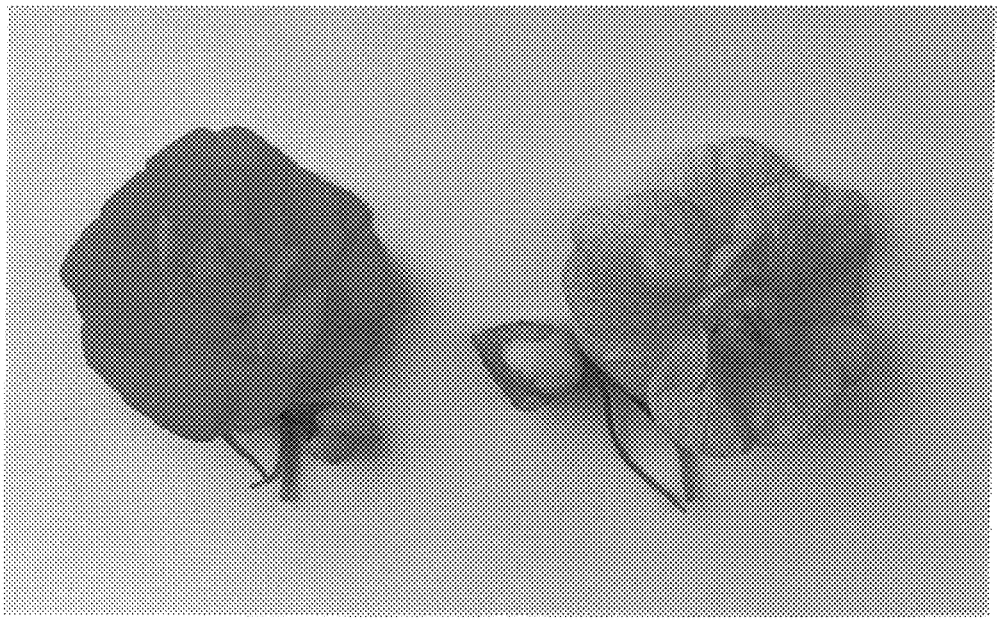

* * * * *